United States Patent [19]
Daigo et al.

[11] Patent Number: 4,659,384
[45] Date of Patent: Apr. 21, 1987

[54] GALLIUM ALLOY FOR DENTAL RESTORATIONS

[75] Inventors: Yasuhito Daigo, Tokyo; Takashi Horibe, Fukuoka; Kengo Inage; Shigeyasu Naruse, both of Chigasaki; Takashi Nara, Abiko; Yoshizo Okamoto, Kitakyushu; Hironobu Yamamoto, Musashino, all of Japan

[73] Assignee: Tokuriki Honten Company, Limited, Tokyo, Japan

[21] Appl. No.: 746,883

[22] Filed: Jun. 20, 1985

[30] Foreign Application Priority Data

| Sep. 7, 1984 [JP] | Japan | 59-187524 |
|---|---|---|
| Sep. 7, 1984 [JP] | Japan | 59-187525 |
| Sep. 7, 1984 [JP] | Japan | 59-187527 |
| Sep. 7, 1984 [JP] | Japan | 59-187528 |
| Sep. 7, 1984 [JP] | Japan | 59-187530 |
| Sep. 7, 1984 [JP] | Japan | 59-187531 |
| May 14, 1985 [JP] | Japan | 60-102375 |

[51] Int. Cl.$^4$ .............. A61K 5/01; C22C 28/00; C09K 3/00
[52] U.S. Cl. .............. 106/35; 433/228.1; 420/555
[58] Field of Search .............. 106/35; 420/555; 433/228.1

[56] References Cited

FOREIGN PATENT DOCUMENTS

| 0101208 | 8/1975 | Japan | 420/555 |
|---|---|---|---|
| 0048091 | 12/1980 | Japan | 420/555 |
| 0135548 | 7/1985 | Japan | 420/555 |
| 354938 | 11/1972 | U.S.S.R. | 420/555 |

*Primary Examiner*—Nancy Swisher
*Attorney, Agent, or Firm*—Oblon, Fisher, Spivak, McCelland & Maier

[57] ABSTRACT

A gallium alloy for dental restorations which is hardenable at mouth temperature or around 37° C. or more after triturating multicomponent liquid gallium alloy with alloy powder, is disclosed. The mixture has a heterogeneous structure after hardening, and contains as the overall composition, 9–47% gallium, 1–35% indium, 0.2–38% tin and 1–68% silver as indispensable components and one or more elements selected from 0.4–35% palladium, 0.5–25% copper and 0.4–12% zinc as arbitrary components. The multicomponent liquid gallium alloy contains 45–85% gallium, 5–40% indium and 1–30% tin as fundamental components and small amounts one or more elements selected from silver, palladium, gold, platinum, copper, zinc and germanium as arbitrary components. The alloy powder contains 1–85% silver and two or more elements selected from 1–40% tin, 1–40% palladium, 1–30% copper, 1–15% zinc and 1–25% indium. Also, the alloy powder is used with one or more single metal powder selected from palladium, platinum, gold, silver, copper and tin and/or powdered alloy containing one or more of said metals in which said single metal powder and said powdered alloy consist of a spherical or near spherical–irregular particle shape having particle size different from those of said alloy powder or a flat or flaky particle shape.

10 Claims, 1 Drawing Figure

GALLIUM ALLOY FOR DENTAL RESTORATIONS

BACKGROUND OF THE INVENTION

1. Field of the Invention

This invention relates to a gallium alloy for dental restorations, and particularly to a powder-liquid mixture containing a gallium alloy which is hardenable after triturating a liquid gallium alloy with a metal powder, especially a silver base alloy powder, applied for the purpose of replacing dental amalgam containing mercury.

2. Discussion of the Background

A dental amalgam as a hardenable mixture is prepared by mixing liquid mercury with a silver alloy powder. This amalgam is filled into a tooth cavity, and hardened at mouth temperature by an amalgam reaction between mercury and silver or other components yielding strength durable to occlusal pressure. Since the amalgam has good workability in preparation, it has long been used up to the present.

However, as to mercury the toxicity of its vapor has been formerly known, and environmental pollution caused by mercury has recently become a social problem in many countries.

Suggestions of using gallium in place of mercury date as far back as 1928 and subsequent attempts have been made, because gallium has a melting point (mp. 29.78° C.) next lower to that of mercury (m.p. −38.86° C.).

From a metallurgical viewpoint, gallium constitutional diagrams are known for binary systems such as Ga-Zn (eutectic temperature 25° C.), Ga-Sn (eutectic temp. 20° C.) and Ga-In (eutectic temp. 15.7° C.). However, gallium ternary systems have been scarcely known.

Most research concerning non-mercury metal filling materials for dental application has been made using gallium metal or gallium binary eutectic alloys known as Ga-Sn, Ga-Zn and Ga-In together with powder such as palladium, silver, gold, copper, tin, zinc and silver-tin-copper alloy. Of these, J. P. Lyle et al. disclosed in U.S. Pat. No. 2,585,393 (1952) an alloy composed of 49–74% nickel, 25–45% gallium and 0.5–7.5% silicon as a metallic composition, prepared by admixing a powder mixture of nickel and silicon with a proper portion of gallium by warming it slightly to form a liquid.

D. L. Smith et al. reported a compound for filling teeth cavities containing 27–31% gallium, 29–30% tin and 40–43% copper, by preparing Ga-Sn eutectic alloy with powdered copper-tin alloy ($Cu_3Sn$) in *The Journal of the American Dental Association*, Vol. 53, P 677 (1956) and also disclosed an alloy consisting of 20–40% of liquid gallium and 60–80% powdered cobalt in U.S. Pat. No. 2,864,695 (1958).

S. T. Rogova et al. disclosed similar alloy of Ga-Sn-Cu system in U.S. Pat. No. 4,015,981 (1977).

R. M. Waterstrat reported gallium-palladium-tin alloy for restorative dentistry in *The Journal of the American Dental Association*, Vol. 78, P 536 (1969).

In Japanese Pat. No. 1,059,723 (Japanese Patent Publication No. 48091/1980), T. Yoshida claimed a method of preparation of metal filling materials for dental restorations which comprises adding 1–13.5% tin and less than 24.5% indium or less than 5% zinc to gallium so as to lower the melting point of gallium temporarily when triturating them with metal powder. Furthermore, Japanese Pat. No. 1,075,467 (Japanese Patent Publication No. 15453/1981) disclosed alloy powder to be mixed with a binary alloy consisting of gallium and 1–13.5% tin. In these patents, examples are shown relating to the combinations of Ga-Sn binary alloys with single metal powder such as Ag, Au, Cu and Sn or alloy powder such as $Cu_3Sn$, Ag-Cu-Sn and that consisting of 85–55% silver and 15–45% copper to which one or more of (i) less than 15% gold, (ii) less than 15% palladium and (iii) less than 30% tin are further added. However, no examples concerning filling material or hardened product comprising an alloy powder with a ternary or higher liquid gallium alloy having a melting point lower than the eutectic temperature (15.7° C.) of Ga-In alloys were presented in these patents.

The fact that the filling materials containing gallium for dental restorations have not been commercialized up to the present is due to the facts that the melting point of gallium alloys could not be lowered to a practical level, that gallium alloys are difficult in handling and workability as compared with conventional amalgams, and that various properties are not satisfactory for dental restorative materials. In view of the facts, the applicant has engaged in research and development concerning multicomponent liquid gallium alloys as described in Japanese Patent Application Nos. 58-240933 to 58-240936, and others.

SUMMARY OF THE INVENTION

In view of the prior art described above, the invention provides hardenable mixtures for dental restorations which comprise a mixture of a ternary or higher multicomponent liquid gallium alloy having a melting point lower than the eutectic temperature of Ga-In alloy and silver base alloy powder and are hardened relatively rapidly at mouth temperature or around 37° C. or more. The inventors found that a hardenable mixture having a heterogeneous structure after hardening, and containing, as an overall composition (% means wt.% hereinafter), 9–47% gallium, 1–35% indium, 0.2–38% tin and 1–68% silver as indispensable components and one or more of 0.4–35% palladium, 0.4–25% copper and 0.4–12% zinc as arbitrary components and if necessary, one or more of small amounts of gold, platinum and germanium has various properties suitable for use in dental restorations.

The said multicomponent liquid gallium alloy essentially contains 45–85% gallium, 5–40% indium and 1–30% tin as the fundamental components. Also, the said alloy powder contains 1–85% silver and two or more elements selected from the group consisting of 1–40% tin, 1–40% palladium, 1–30% copper, 1–15% zinc and 1–25% indium.

DETAILED DESCRIPTION OF THE PREFERRED EMBODIMENTS

Figure 1:
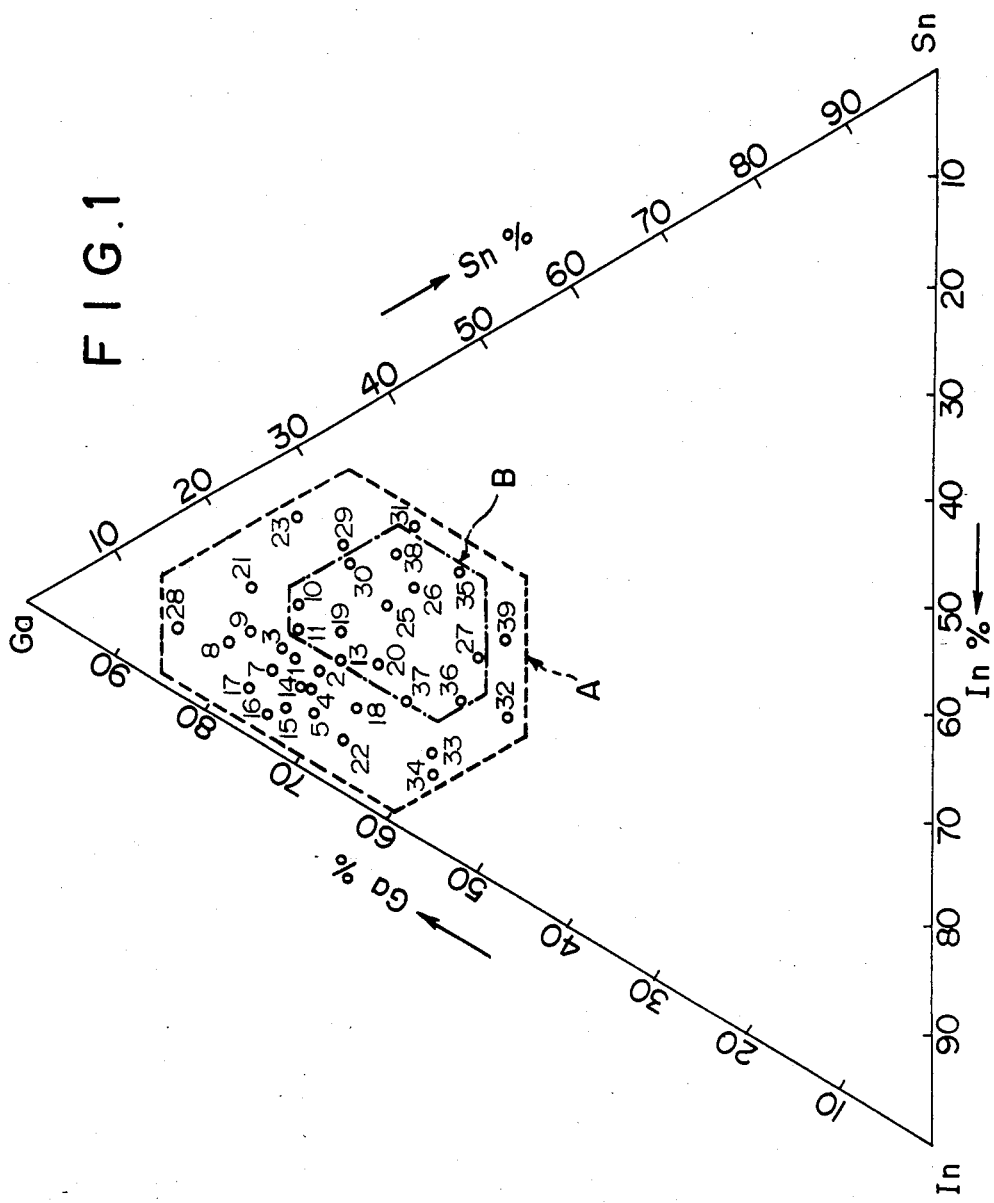
FIG. 1 shows a ternary concentration diagram for gallium, indium and tin, which are fundamental components of the liquid alloy of the invention. In the drawing, an example of liquid alloy is plotted by a mark "O". The figure attached to the mark "O" shows the number of liquid alloy listed in Table 1. Area A encircled by a broken line (- - - - -) indicates the range of composition of a liquid alloy which is used in the invention, and area B encircled by a dot and dash line (—. —) indicates the much preferable range of composition of the liquid alloy.

The invention is basically composed of the following three requirements.

(1) The mixtures after hardening should have a composition and properties suitable for use in dental restorations. Mixture or hardened mixture is called "gamalgam" herein.

(2) The multicomponent liquid gallium alloys should maintain liquid state at ordinary temperature and contain no mercury.

(3) Alloying reaction called "gamalgamation" herein should start by trituration operated at ordinary temperature using the liquid alloy and the metal powder (including alloy powder), and the mixture should relatively rapidly be hardened at a temperature of around 37° C. or more, the same condition as in the oral cavity.

It was found that the powder-liquid mixtures for satisfying these requirements should have a heterogeneous structure after hardening in which unreacted powder particles surrounded by diffusion layer are embedded by gamalgamated liquid alloy matrix and that the material strength of the resultant mixture depends upon that of the powder particles themselves. Specifically, it was found that a mixture containing 9–47% gallium, 1–35% indium, 0.2–38% tin and 1–68% silver as indispensable components and one or more elements selected from 0.4–35% palladium, 0.4–25% copper and 0.4–12% zinc and also if necessary, small amounts of one or more elements selected from gold, platinum and germanium as arbitrary components have various properties such as an adequate hardness, good compressive strength and corrosion resistance and dimensional stability required for dental restorative materials.

The range of composition of the mixture hardened was determined on the basis of experimental results. The requirements and the major functions of elements each is described below. The gallium content should preferably be small, because it has the worst corrosion resistance of the elements in this system. Hardened product No. S2 (see Table 4) which contains 45.2% gallium gave not so good results, although it contains 13.6% palladium. Besides, a hardened product containing 50% gallium showed corrosion resistance worse than that of conventional amalgams. Hardened product No. S22 which contains 9.4% gallium showed a relatively rapid hardening speed, and was judged to be close to a limit for practical use. On the other side, indium and tin also take part in gamalgamation with silver, copper, zinc and palladium and solidification, in which they effect each other to contribute to the mechanical properties of the final products. The range of each component was determined on the basis of experimental results (Table 4). Palladium has a good effect upon the acceleration of hardening speed and the improvement of corrosion resistance but has a tendency to increase setting expansion. The upper limit was determined while taking dimensional change and price into consideration.

The second requirement of the invention is to obtain a mercury-free multicomponent alloy, which has a melting point lower than the eutectic temperature (15.7° C.) of Ga-In alloy and has fluidity at ordinary temperature, by addition of the third component to the Ga-In alloy having the lowest binary eutectic temperature and satisfying the above requirements. Tin which can be easily alloyed with gallium and indium to give lower binary eutectic temperatures, has been considered to be most promising as the third component. So, investigations have been carried out by using gallium, indium and tin as the fundamental elements. As a result, it was confirmed by experiments that an alloy having a composition of 45-85% gallium, 5-40% indium and 1-30% tin has a solidification-initiating point of −3° to −10° C. or less in a semi-stable condition, i.e., it has fluidity at −3° to −10° C. or less in a semi-stationary state, and that the condition continues for a considerable period of time until the condition returns to a stationary state to show its own melting point of 15° C. or less. The similar phenomenon is known as the so-called supercooling in case of pure gallium.

Addition of small amounts (0.01-5%) of the fourth components or more such as silver, palladium, gold, platinum, copper, zinc and germanium, etc. to the above basic liquid alloy having ternary components has been confirmed to be effective for an improvement in the properties of resultant products after hardening though it has been found to have no particular influence on an improvement in fluidity. Addition of supplementary powder to alloy powder, which will be described later, has been found to be also effective for an improvement in the properties of mixture hardened. The elements used for the fourth components or more are not necessarily required to give complete alloy with the fundamental elements forming a homogeneous liquid phase. If the elements can improve the properties of a matrix (will be described later) after hardening without hindering the fluidity, they may be used as the fourth component or more. It was found that rhodium, iridium, osmium and ruthenium of the platinum group and tantalum, titanium, molybdenum, tungsten, magnesium, bismuth and aluminium may also be used as the fourth component or more. These elements may be added alone or in combination with silver, palladium, gold, platinum, copper, zinc and germanium as described above.

The third requirement of the invention is to develop a metal powder which relatively rapidly initiates hardening after mixing with the liquid gallium alloy in a manner similar to conventional amalgam fillings.

It is required that alloying reaction will be activated by the degree of heat generated upon mixing the liquid gallium alloy with the metal powder (including alloy powder) by means of mixing apparatus (e.g. Amalgamator HIMIX VS III by GC Co.). The said metal powder must also satisfy the requirements that the resulting mixture hardens upon standing sufficiently at mouth temperature for dental restorations.

Those elements such as tin, palladium, copper, zinc, indium and silver which can easily be alloyed with gallium indium and tin, which are the fundamental elements of the liquid alloy have been found suitable for the metal powder of this purpose. As to the composition of these elements, specific alloy powder containing as the fundamental elements 1-85% silver and two or more elements selected from 1-40% tin, 1-40% palladium, 1-30% copper, 1-15% zinc and 1-25% indium has been found suitable. If an alloy powder contains palladium in large quantity, it is advantageous in terms of corrosion resistance and acceleration for hardening, however, it is disadvantageous in terms of setting expansion and cost. Thus, the content of palladium should preferably be less than 40%. As to tin, copper, indium and silver, the composition has been determined on the basis of experimental results concerning the corrosion resistance and mechanical properties such as hardness and brittleness of the mixture hardened. The reason that a minimum of three constitutional elements (two elements in addition to silver) are required for the said alloy powder is because the degree of freedom of combination is too small in the binary system to obtain sufficient mechanical strength for the particles themselves as the case where binary, brittle materials such as Ag-Sn and soft materials such as Ag-Zn and Ag-In are disadvantageously included in the objects for selection. Also, Ag-Pd alloy powder has good corrosion resistance and fairly good mechanical properties, but it is much inferior to Ag-Pd-Cu alloy powder. The experimental results also have shown that the hardened products (S11, S21) using an alloy powder of Ag-Pd-Cu system, (S36) using an alloy powder of Ag-Sn-Cu system and (S43) using an alloy powder of Ag-Cu-Zn system each have a compressive strength satisfying the standard value (described later).

The invention also refers to alloy powder containing gold, platinum and iridium to increase the nobility. In addition to gold, platinum and iridium, the elements such as bismuth, magnesium, nickel, antimony and titanium which do not adversely affect gamalgamation with gallium and do not extremely increase the hardness if added to the above alloy powder, may also be added.

It has been found that the workability at mixing is satisfactory and the hardened products have relatively greater strength if the metal powder is spherical (including a sphere) or near spherical-irregular shape. So, those particles mainly consisting of spherical or near spherical-irregular shape of particles are employed in the invention.

In addition to the main metal powder as described above, other metal powders having different components and shapes, e.g., flat or flaky metal powder or spherical or near spherical-irregular metal powder having a particle size different from that of the main metal powder, have been found to be useful for not only accelerating gamalgamation of the matrix and improving the corrosion resistance and the strength, but also improving mixing workability and controlling solidification speed. The elements such as palladium, platinum, gold, silver, copper and tin have been found suitable for these supplemental metal powder additives as single metals or alloys.

An important effect of the addition of supplementary metal powder is to gamalgamate precious metals in a gallium-rich matrix of hardened products. For this purpose, noble metals such as palladium, platinum, gold and silver are most suitable. These noble metals form a solid solution with or disperse into the components of the gallium-rich matrix phase, and play a role of improving corrosion resistance. In order to effect alloying of the matrix with smaller amounts of the precious metals, the use of the supplementary powder of fine and flaky particles are preferable and advantageous. As to copper, tin and zinc, they are considered to be useful for controlling the solidification speed and improving the workability rather than for improving the corrosion resistance. Addition of an alloy consisting of these elements is effective to improve the packing density of particles and the powder-liquid ratio as well as the above basic effects. Therefore, flat or flaky particles contribute to an improvement in corrosion resistance and spherical particles contribute to an improvement in mechanical properties, so that a balance of the two shapes is required in improving workability.

Features of the invention are described below with reference to the examples.

EXAMPLE 1

In this example the liquid alloys and metal powders used for the invention are described.

Table 1 shows examples of liquid alloys used for the hardenable mixtures of the invention and their melting points.

FIG. 1 shows ternary concentration diagrams for gallium, indium and tin, the fundamental elements of the liquid alloys of the invention.

TABLE 1

Examples of Fundamental Liquid Alloys and Compositions

| No. | Component (%) | | | Melting Point (°C.) |
|---|---|---|---|---|
| | Ga | In | Sn | |
| L 1 | 70 | 20 | 10 | 11 |
| 2 | 67.5 | 22.5 | 10 | 11.5 |
| 3 | 72 | 18 | 10 | 11 |
| 4 | 68 | 24 | 8 | 12 |
| 5 | 68 | 26 | 6 | 13.2 |
| 6 | 69 | 24.5 | 6.5 | 12.5 |
| 7 | 72.5 | 20 | 7.5 | 12 |
| 8 | 75 | 17.5 | 7.5 | 13.5 |
| 9 | 75 | 15 | 10 | 12 |
| 10 | 70 | 15 | 15 | 10 |
| 11 | 70 | 17.5 | 12.5 | 10 |
| 12 | 67.5 | 20 | 12.5 | 9 |
| 13 | 65 | 22.5 | 12.5 | 10 |
| 14 | 69.1 | 23.3 | 7.6 | 12 |
| 15 | 71.3 | 24.1 | 4.6 | 13.5 |
| 16 | 73.3 | 23.8 | 2.9 | 15.0 |
| 17 | 74.5 | 20.9 | 4.6 | 13.6 |
| 18 | 64 | 28 | 8 | 12 |
| 19 | 65 | 20 | 15 | 10 |
| 20 | 61 | 25 | 14 | 10 |
| 21 | 75 | 11 | 14 | 12 |
| 22 | 65 | 30 | 5 | 13 |
| 23 | 70 | 7 | 23 | 15 |
| 24 | 53 | 20 | 27 | 10 |
| 25 | 60 | 20 | 20 | 10.5 |
| 26 | 57 | 20 | 23 | 10 |
| 27 | 50 | 30 | 20 | 10 |
| 28 | 83 | 11 | 6 | 15 |
| 29 | 65 | 12 | 23 | 12 |
| 30 | 64 | 14 | 22 | 10 |
| 31 | 57 | 14 | 29 | 15 |
| 32 | 47 | 37 | 16 | 15 |
| 33 | 55 | 37 | 8 | 12 |
| 34 | 55 | 38 | 7 | 15 |
| 35 | 52 | 21 | 27 | 10 |
| 36 | 52 | 33 | 15 | 10 |
| 37 | 58 | 30 | 12 | 10 |
| 38 | 59 | 16 | 25 | 10 |
| 39 | 47 | 30 | 23 | 12 |

The liquid alloys of the invention have been prepared first by compounding the predetermined amounts of gallium and indium, and heating the mixture in a Teflon beaker at about 200° C. to give homogeneous alloy, then by adding a predetermined amount of tin and, if required, the fourth components such as silver, palladium, gold, platinum, copper, zinc and germanium, and by stirring the resulting mixture well with heating to form the liquid alloys. The liquid alloys were stored in bottles at ordinary temperature ready to use at need.

As can be seen from Table 1, each of these liquid alloys has a melting point of 15° C. or less which is lower than the eutectic temperature of Ga-In alloy. Zone A encircled by a broken line (- - - -) in FIG. 1 indicates an area showing such a melting point, and zone B encircled by a dot and dash line (—. —) indicates an area showing a melting point of less than 10° C. of the liquid alloys. These alloys showed fluidity at a temperature below the melting points in Table 1, although it was in a semi-stable state. As to cooling characteristics measured for these liquid alloys, when liquid alloy L 19 in Table 1 was cooled in a refrigerator, the temperature of the liquid alloy decreased with a decrease in the temperature of the refrigerator. The liquid alloy maintained the fluidity in a semi-stable state for 72 hrs even at −7° C. But, the duration of the semi-stable state varies and can be considerably extended with the conditions of production and storage of the liquid alloy. Solidification-initiating temperature for the above liquid alloy varies from −3° to −10° C. or less with the conditions of production. The semi-stable state may also be eliminated by applying a cycle of heating and solidification one or several times to the liquid alloy.

Table 2 shows examples of liquid alloys in which the fourth components or more were added to the fundamental ternary alloys.

TABLE 2

Examples of Liquid Alloys Containing the Fourth Components, or more

| No. | Composition of Liquid Alloys |
|---|---|
| L2X | 3% gold added to L2 as the fourth component |
| L5X | 3% zinc added to L5 as the fourth component |
| L7X | 1% palladium, 2% silver and 2% gold added to L7 as the fourth, fifth and sixth components |
| L13X | 0.5% palladium and 5% silver added to L13 as the fourth and fifth components |
| L19X | 0.5% platinum added to L19 as the fourth component |
| L25X | 4% zinc and 0.1% copper added to L25 as the fourth and fifth components |
| L25Y | 0.5% silver and 0.1% germanium added to L25 as the fourth and fifth components |
| L26X | 0.5% silver added to L26 as the fourth component |
| L35X | 0.08% silver and 0.02% germanium added to L35 as the fourth and fifth components |

As shown in Table 2, the liquid alloys containing small amounts of one or more elements selected from silver, palladium, gold, platinum, copper, zinc and germanium showed fluidity at 15° C. or less, and showed solidification behaviors similar to those of the basic ternary alloys. These liquid alloys will be described later.

Thus, the liquid alloys have fluidity at ordinary temperature. However, since the liquid alloys might be in solidified or semi-fused conditions at a cold nothern district, tests have been made on the mixing properties and workability by applying the liquid alloys after being given the repeated cycle of solidification and fusion. The results, however, have not shown any disadvantages.

Metal powder to be mixed with the above liquid alloys is described below.

Production of metal powder includes chemical reduction, coprecipitation, electrolysis, vacuum vapor deposition, atomization, shot process, crushing, cutting, etc. Of these, atomization is mainly used in yielding spherical or near spherical-irregular particles with a particle size of about 100μ or less suitable for the invention. If the metal particles received surface oxidation, they should preferably be subjected to reduction at low temperatures in a furnace in an atmosphere of hydrogen for deoxidation. Also, flat or flaky metal powders were prepared by cutting process, or by treating chemically reduced powder or atomized powder in a ball mill. The metal powder particles classified by sieving or elutriation, if required, were used by blending them adequately.

Table 3 shows examples and compositions of alloy powders prepared in a manner as described above.

TABLE 3

Examples of Alloy Powder and Compositions Thereof

| No. | Component (%) | | | | | | | | |
|---|---|---|---|---|---|---|---|---|---|
| | Pd | Ag | Sn | Cu | Zn | In | Au | Pt | Ir |
| P1 | 30 | 6 | 36 | 28 | | | | | |
| P2 | | 60 | 25 | 15 | | | | | |
| P3 | 15 | 36 | 27 | 3 | 2 | 4 | 12 | 0.9 | 0.1 |
| P4 | 26 | 33 | 25 | 15 | 1 | | | | |
| P5 | 35 | 24 | 5 | | 12 | 24 | | | |
| P6 | 1 | 25 | 38 | 20 | | 16 | | | |
| P7 | | 65 | 20 | 10 | | 5 | | | |
| P8 | 10 | 48 | 26 | 14 | | 2 | | | |
| P9 | 25 | 58 | | 15 | 2 | | | | |
| P10 | 2 | 80 | | 18 | | | | | |
| P11 | 40 | 30 | | 30 | | | | | |
| P12 | 4 | 72 | 10 | 6 | 8 | | | | |
| P13 | 8 | 64.5 | 10 | 12 | 3.5 | 1 | | 1 | |
| P14 | 25 | 54 | | 16 | 5 | | | | |
| P15 | | 70 | | 20 | 10 | | | | |

Such alloy powder basically comprises those components which can be easily alloyed with gallium, indium and tin, the fundamental components of the liquid alloys, and contains 1–85% silver and at least two elements selected from 1–40% tin, 1–40% palladium, 1–30% copper, 1–15% zinc and 1–25% indium. The alloy powder may contain gold, platinum, iridium, etc. as shown at P3 in Table 3 or any components other than those illustrated in Table 3, if they do not impair the fundamental properties of the invention, i.e., if hardening proceeds relatively rapidly and the hardened products have satisfactory properties for dental restorative materials.

If otherwise noted, the shapes of alloy powder used are spherical, or near spherical-irregular.

EXAMPLE 2

In this example, hardened products comprising various combinations of the liquid alloys and the metal powder described in Example 1 are described.

The hardened products have been prepared by putting the alloy powder (1 g) and the liquid alloy (0.25–1.2 g) into a capsule, mechanically triturating the admixture at ordinary temperature for 5–15 seconds by means of an amalgamator (HIMIX VS III made by GC Co.), packing the resultant mixture in a mold, and then maintaining the mold at 37±1° C. in an incubator.

Table 4 shows examples and compositions of the hardened products of the invention.

TABLE 4

Examples of Hardened Products and Compositions Thereof

| Hardened Products No. | Components (%) | | | | | | | | | Remarks | | |
|---|---|---|---|---|---|---|---|---|---|---|---|---|
| | Ga | In | Sn | Ag | Pd | Cu | Zn | Au | Pt | Others | Corrosion Resistance | Metal Powder | Liquid Alloy |
| S1 | 25.2 | 10.3 | 26.9 | 3.5 | 17.6 | 16.5 | | | | | | P1 | L20 |
| S2 | 45.2 | 6 | 19.6 | 2.7 | 13.6 | 12.7 | | | | | Δ | P1 | L28 |
| S3 | 22.6 | 15.6 | 24.2 | 3.5 | 17.6 | 16.5 | | | | | | P1 | L34 |

TABLE 4-continued

Examples of Hardened Products and Compositions Thereof

| Hardened Products No. | Components (%) | | | | | | | | | Remarks | | |
|---|---|---|---|---|---|---|---|---|---|---|---|---|
| | Ga | In | Sn | Ag | Pd | Cu | Zn | Au | Pt | Others | Corrosion Resistance | Metal Powder | Liquid Alloy |
| S4 | 26.8 | 9.3 | 5.1 | 33.7 | 14.5 | 8.8 | 1.2 | | 0.6 | | ◉ | P9L | L13 |
| S5 | 30 | 31.6 | 6.1 | 10.9 | 15.9 | | 5.5 | | | | | P5 | L34 |
| S6 | 24.7 | 8.2 | 22.9 | 35.3 | | 8.8 | | | | | ○ | P7 | L25 |
| S7 | 25.1 | 19.6 | 28.2 | 14.7 | 0.6 | 11.8 | | | | | ○ | P6 | L20 |
| S8 | 11.4 | 15.6 | 36.2 | 20 | 0.8 | 16 | | | | | | P6 | L31 |
| S9 | 12.2 | 5 | 2.8 | 64 | 1.6 | 14.4 | | | | | | P10 | L20 |
| S10 | 28.8 | 6.2 | 20.9 | 35.3 | | 8.8 | | | | | | P2 | L10 |
| S11 | 24.7 | 8.2 | 8.2 | 47.1 | 1.2 | 10.6 | | | | | ○ | P10 | L25 |
| S12 | 23.5 | 19.9 | 14.8 | 14.1 | 20.6 | | 7.1 | | | | ◉ | P5 | L31 |
| S13 | 28.3 | 18.7 | 32 | 11.4 | 0.5 | 9.1 | | | | | | P6 | L35 |
| S14 | 29.9 | 8.2 | 17.8 | 35.3 | | 8.8 | | | | | x | P2 | L7 |
| S15 | 27.8 | 9.3 | 17.5 | 34 | 3.4 | 8.0 | | | | | ◉ | P2PSAP | L2 |
| S16 | 36.8 | 14.1 | 17.7 | 16.4 | 6.8 | 1.4 | | 0.9 | 5.5 | 0.4 Ir 0.05 | ◉ | P3 | L2 |
| S17 | 21.4 | 8.6 | 11.1 | 33.6 | 15.6 | 8.5 | 1.2 | | | Ge 0.01 | ◉ | P9PS | L35X |
| S18 | 26.6 | 8.2 | 6.2 | 31.8 | 14.7 | 9.4 | 2.9 | | 0.2 | | ◉ | P14 | L19X |
| S19 | 26.8 | 8.2 | 20.9 | 19.4 | 15.3 | 8.8 | 0.6 | | | | ◉ | P4 | L19 |
| S20 | 28.5 | 7.8 | 2.9 | 34.9 | 15.1 | 8.8 | 1.2 | 0.8 | | | ◉ | P9 | L7X |
| S21 | 26.9 | 9.3 | 5.1 | 17.6 | 23.5 | 17.6 | | | | | ◉ | P11 | L13 |
| S22 | 9.4 | 6 | 4.6 | 64 | 1.6 | 14.4 | | | | | | P10 | L39 |
| S23 | 23.5 | 5.8 | 17.8 | 42.3 | 2.4 | 3.5 | 4.7 | | | | ◉ | P12 | L31 |
| S24 | 26.8 | 8.2 | 27.4 | 3.5 | 17.6 | 16.5 | | | | | | P1 | L19 |
| S25 | 26.8 | 8.2 | 23.9 | 2.9 | 24.5 | 13.7 | | | | | | P1P | L19 |
| S26 | 24.8 | 9.4 | 23.2 | 27.6 | 6.9 | 8.1 | | | | | ◉ | P8P | L25 |
| S27 | 13.8 | 3.8 | 25.4 | 4.4 | 33.6 | 18.6 | | 0.4 | | | | P1P | L7X |
| S28 | 34.2 | 4.5 | 17.2 | 35.3 | | 8.8 | | | | | x | P2 | L28 |
| S29 | 26.8 | 8.2 | 7.6 | 33.3 | 14.3 | 8.6 | 1.2 | | | | ◉ | P9T | L19 |
| S30 | 26.6 | 8.2 | 6.1 | 33.7 | 14.6 | 8.8 | 1.2 | | 0.8 | | ◉ | P9L | L19X |
| S31 | 11.4 | 23.0 | 7.8 | 19.2 | 28 | 0.2 | 10.4 | | | | | P5 | L25X |
| S32 | 29.9 | 8.2 | 8.9 | 42.4 | 2.4 | 3.5 | 4.7 | | | | △ | P12 | L7 |
| S33 | 29.9 | 8.2 | 3.1 | 33.5 | 15.6 | 8.5 | 1.2 | | | | ◉ | P9PS | L7 |
| S34 | 24.5 | 8.2 | 22.6 | 19.2 | 15.0 | 8.9 | 0.6 | 0.9 | | Ge 0.04 | ◉ | P4GCA | L25Y |
| S35 | 11.4 | 3.8 | 3.8 | 24 | 32 | 24.2 | 0.8 | | | | | P11 | L25X |
| S36 | 26.8 | 8.2 | 20.9 | 35.3 | | 8.8 | | | | | ○ | P2 | L19 |
| S37 | 26.8 | 9.3 | 5.1 | 34.1 | 14.7 | 8.8 | 1.2 | | | | | P9 | L13 |
| S38 | 26.8 | 8.2 | 21.8 | 34.6 | | 8.6 | | | | | ○ | P2T | L19 |
| S39 | 14 | 1.4 | 24.6 | 48 | | 12 | | | | | | P2 | L23 |
| S40 | 27 | 23.1 | 6.9 | 14.1 | 20.6 | | 7.1 | 1.2 | | | ◉ | P5 | L2X |
| S41 | 34.2 | 4.5 | 15.4 | 30.7 | 7.6 | 7.6 | | | | | ○ | P2P | L28 |
| S42 | 26.8 | 9.3 | 19.8 | 35.3 | | 8.8 | | | | | △ | P2 | L13 |
| S43 | 24.7 | 8.2 | 8.2 | 41.2 | | 11.8 | 5.9 | | | | ○ | P15 | L25 |
| S44 | 27.2 | 24.5 | 5.3 | 14.1 | 20.6 | | 8.3 | | | | | P5 | L5X |
| S45 | 14.6 | 4.8 | 0.6 | 24 | 32 | 24 | | | | | | P11 | L16 |
| S46 | 30.9 | 6.2 | 18.8 | 35.3 | | 8.8 | | | | | x | P2 | L9 |
| S47 | 26.8 | 8.2 | 6.2 | 34.1 | 14.7 | 8.8 | 1.2 | | | | ◉ | P9 | L19 |
| S48 | 26.8 | 9.3 | 18 | 30.7 | 7.6 | 7.6 | | | | | ○ | P2P | L13 |
| S49 | 25.4 | 8.8 | 17.7 | 32.7 | 7.8 | 7.6 | | | | | ◉ | P2P | L13X |
| S50 | 26.8 | 8.2 | 19.1 | 30.7 | 7.6 | 7.6 | | | | | ◉ | P2P | L19 |
| S51 | 28.5 | 7.8 | 8.8 | 43.1 | 2.8 | 3.5 | 4.7 | 0.8 | | | ◉ | P12 | L7X |
| S52 | 26.8 | 8.2 | 6.2 | 33.5 | 15.6 | 8.5 | 1.2 | | | | | P9PS | L19 |
| S53 | 26.4 | 11.5 | 24.5 | 3.5 | 17.6 | 16.5 | | | | | | P1 | L18 |
| S54 | 26.8 | 8.8 | 12.1 | 37.8 | 4.7 | 7.1 | 2.1 | | 0.6 | | ◉ | P13 | L19 |
| S55 | 28.5 | 9.6 | 3.1 | 34.1 | 14.7 | 8.8 | 1.2 | | | | ◉ | P9 | L14 |
| S56 | 26.8 | 9.3 | 19.5 | 19.4 | 15.8 | 8.6 | 0.6 | | | | ◉ | P4PSA | L13 |
| S57 | 20.6 | 12.4 | 29.4 | 3.5 | 17.6 | 16.5 | | | | | ◉ | P1 | L27 |
| S58 | 12.3 | 4.3 | 2.4 | 64.9 | 1.7 | 14.4 | | | | | | P10 | L13X |
| S59 | 23.5 | 5.8 | 11.9 | 34.1 | 14.7 | 8.8 | 1.2 | | | | | P9 | L31 |

The properties of the hardened products have been evaluated according to a method of evaluation as described below. Evaluation of corrosion resistance is noted by symbols x, △, ○, and ◉ (better in the descending order), and the results are illustrated in Table 4. Mechanical properties were investigated according to JIS T 6109 (Japanese Industrial Standards for dental amalgam alloy). Compressive strength was measured according to the American Dental Association (hereinafter referred to as ADA) Standards (8.16 kgf/mm² or more after 1 hr and 25 kgf/mm² or more after 24 hrs). Decoloration tests were carried out according to JIS T 6108 (for dental silver casting alloy).

The results of evaluation for the hardened products listed in Table 4 have almost satisfied the above standards. Also, the structure and properties of the hardened products are described in detail in the examples below.

As the results of investigations for the behavior of dimensional changes, the hardened products have no problem for the JIS standards, since they have an expanding tendency. However, all of them have not satisfied the ADA standards (dimensional changes: ±20 μm/cm). For example, S37 showed a large expansion of +160 to +220 μm/cm, and S19 showed a relatively small expansion of +60 to +80 μm/cm. If the compositions of S37 and S19 are compared, the palladium contents are almost the same, but there was a difference in the tin contents (the tin content of S37 was about ¼ that of S19). S38 (+12 to +18 μm/cm) containing no palladium satisfied the ADA standards.

As a clinical test, S37 which showed the largest setting expansion was filled into the cavities in extracted human teeth, but it had no harmful effect without causing the generation of crack or fracture of the teeth.

The reason why such large setting expansion did not cause any harmful effect can be explained by the behavior of dimensional changes measured. That expansion, though large, occurs relatively in a short time while the mixture is still soft as plastic mass.

Therefore, it is considered that the hardened products of this invention do not necessarily need to meet the specification for a conventional amalgam for the reason described above.

Next, mechanical strength of the hardened products is described as follows. Hardening of the hardened products of the invention is considered to proceed by such a mechanism that gamalgamation occurs by diffusion of the components of liquid alloy and the metal powder to each other, and diffusion initiates at the interface between them. Further, EPMA analysis of hardened products has revealed that the relatively large spherical particles have diffusion layers of higher gallium level in their marginal portion, unaffected inner center portion, and gamalgamated phase, i.e. matrix, around them, in which components of powder such as silver, palladium and copper have diffused into the phase mainly consisting of liquid alloy components.

Thus, solidification proceeds and stops by mutual local diffusion between the liquid and the powder without forming complete homogeneous alloy under the condition of relatively low temperature around 37° C. as in the oral cavity.

It is assumed that intermetallic compounds such as $Ag_3Ga$, $PdGa$, $CuGa_2$, $Pd_2In$, $Ag_3In$, $Pd_2Sn$, $Cu_6Sn_5$, etc., have been formed by gamalgamation in the heterogeneous phases except unreacted portions.

Therefore, the composition of hardened products in Table 4 shows the overall composition of the whole structure of hardened products.

Thus, the mechanical strength of hardened products depends considerably upon the mechanical strength of alloy powder particles themselves. High mechanical strength is expected in such a case that the alloy powder particles are spherical, having an adequate hardness, and being charged with high packing density in a gallium-rich matrix. However, particles having excess hardness yield hardened products which are difficult to polish in the clinical operations and injure a tooth at the opposity side. So, a Vickers hardness of about 350 or less has been found to be desirable.

Furthermore, the effect of the shape of metal powder particles to the hardened products is described. Comparison of compressive strength at 24 hrs after mixing has been made between hardened products consisting of spherical P9 and L19 and those consisting of flat P9 and P19 (the same composition as of S37). The result has shown that the former (spherical) has compressive strength of 32.1 kgf/mm², and the latter (flat) 8.5 kgf/mm². There has been a great difference between the two. Cutting powder having both flat particle shape and large particle size gives low rate of hardening. For example, a hardened product (the same composition as of S24) consisting of P1 and L19 has shown the hardness less than Hv 50 even after storage at 37±1° C. for 3 days after mixing. However, improvement of hardness can be made by mixing fine and flaky powder to the said cutting powder. For instance, a hardened product (the same composition as of S25) using P1P, which comprises the above cutting powder and 20% flaky palladium powder of less than 635 mesh has shown the hardness of Hv 65 after 2 hrs, with relatively high rising rate of hardening.

Thus, rate of hardening can be improved even in cutting powder, but spherical powder giving higher packing density is superior to cutting powder in terms of strength of hardened products.

As to corrosion of hardened products, gallium is most corrosive element in the components of the materials of the invention, which has been observed by the behaviors in lactic acid and hydrochloric acid. It has been found that the corrosive tendency of the elements in hardened products is $Ga>>In>Sn>Cu>Zn>Ag>Pd>Au$, Pt, Ir in the order.

Therefore, it has been found preferable, in order to increase corrosion resistance, that the gallium-rich matrix should be gamalgamated with noble metal elements, or that the tin content of the liquid alloy should be increased by reducing the gallium content as much as possible within the range of compositions having acceptable level of melting point.

Thus, taking into account the fluidity as well as other properties which affect the corrosion resistance and the dimentional change of hardened products, composition of liquid alloys basically comprising 49–71% gallium, 12–28% tin and 13–33% indium as illustrated by zone B in FIG. 1 is preferable.

For the main purpose of increasing corrosion resistance of matrix of hardened products by gamalgamation with noble metal or by dispersing them, two methods including addition of the fourth components or more to the liquid alloys and addition of the supplementary powder additives as described above are applied in the invention.

In adding the fourth components or more to the liquid alloys, elements which lower the melting point of the liquid alloys have no trouble if added in large quantities within the allowable range. However, if noble metals are gamalgamated in excess quantities, they cause an increase in melting point. So, noble metals should preferably be dispersed in the form of fine particles into the liquid alloys, or they may separately be added as supplementary powder additives. The latter method is advantageous since the degree of freedom is large. Thus, addition of an element as the fourth element or more to the liquid alloys and addition of the element as a supplementary powder additive have common effect. In both methods, the element is found to be also effective for improving the properties of the hardened products. For example, it contributes to the control of rising rate of hardening, an important factor in clinical operations, and to an improvement in corrosion resistance, dimensional changes, mechanical strength, etc.

As to the strength of hardened products, it has been found that as described above, powder having a function of strengthening of the hardened products should preferably be present in a mixture of various sizes of spherical particles with an adequate size distribution which are useful for raising the packing density and improving the strength. For example, S47 applying metal powder P9 having a size distribution of 10–74μ has a hardness of 240 Hv, this is much superior to conventional products in terms of mechanical strength, and may be used in place of dental cast materials. As moldable materials which are prepared out of the mouth like cast materials, hardening may be promoted under higher temperature of more than 80° C.

From such a viewpoint, micron order of spherical, or near spherical-irregular or flat or flaky palladium, platinum, gold, silver, copper and tin were prepared in the experiments as the supplementary powder additives.

Table 5 shows examples of metal powder containing the supplementary powder additives.

TABLE 5

Examples of metal powder containing supplementary powder additives

| No. | Composition of metal powder |
|---|---|
| P1P | supplementarily adding palladium powder to P1 at a P1:Pd ratio of 1:0.20 |
| P2T | supplementarily adding tin powder to P2 at a P2:Sn ratio of 1:0.02 |
| P2P | supplementarily adding palladium powder to P2 at a P2:Pd ratio of 1:0.15 |
| P2PSAP | supplementarily adding 30% palladium-silver alloy powder and palladium powder to P2 at a P2:30% Pd—Ag:palladium ratio of 1:0.05:0.05 |
| P4GCA | supplementarily adding 75% gold-copper alloy powder to P4 at a P4:75% Au—Cu ratio of 1:0.02 |
| P4PSA | supplementarily adding 70% palladium-silver alloy powder to P4 at a P4:70% Pd—Ag ratio of 1:0.02 |
| P8P | supplementarily adding palladium powder to P8 at a P8:Pd ratio of 1:0.02 |
| P9L | supplementarily adding platinum powder to P9 at a P9:Pt ratio of 1:0.01 |
| P9T | supplementarily adding tin powder to P9 at a P9:Sn ratio of 1:0.025 |
| P9S | supplementarily adding silver powder to P9 at a P9:Ag ratio of 1:0.025 |
| P9PS | supplementarily adding palladium powder to P9 at a P9:Pd ratio of 1:0.025 and adding silver powder to P9 at a P9:Ag ratio of 1:0.01 |

The supplementary powder additives should previously be mixed with the main powder. It saves trouble of weighing in mixing with the liquid alloys. The supplementary powder can be added in different manners other than the above examples. Thus, the invention should not be limited to the said manner, and it is also possible to prepare the liquid alloys, the main powder and the supplementary powder separately when triturating.

Next, various combinations of the liquid alloys containing the fourth components or more and the metal powder containing the supplementary powder additives have been compared with combinations of the liquid alloys containing no additives and the metal powder without any supplements. The difference in their corrosion resistance and the effect of the fourth components or more and the supplementary powder additives are described in detail.

Hardened product S28 (corrosion resistance evaluated as x, corrosion resistance will similarly be illustrated by symbols hereinafter) is a combination of L28 and P2, the liquid of which, L28, has the largest gallium content of 83% of the combinations of the liquid alloys and positions at the gallium-rich side in zone A in FIG. 1. Metal powder P2 containing no noble metals other than 60% Ag has a poor corrosion resistance. Thus, the hardened product S28 showed corrosion resistance of the lowest level of all the hardened products. Hardened product S41 (evaluation: ○), a combination of L28 and metal powder P2P which contains palladium (15% Pd added to P2) as a supplementary powder additive for an improvement of corrosion resistance of the above system, showed markedly higher corrosion resistance than hardened product S28.

Table 4 indicates that corrosion resistance improves from S42 (evaluation: Δ), a combination with P2, to S48 (○), a combination with P2P, in L13 series of combinations, and from S36 (○), a combination with P2, to S50 (○), a combination with P2P, in L19 series of combinations. Such an improvement in corrosion resistance described above is thought to result from alloying the gallium-rich matrix in the hardened products with palladium powder supplementarily added.

It is also seen from Table 4 that corrosion resistance improves from S32 (Δ), a combination with L7, to S51 (○), a combination with L7X, in P12 series of combinations, and from S48 (○), a combination with L13, to S49 (○), a combination with L13X, in P2P series of combinations.

These results indicate that the matrix has been made noble by the dispersion of noble metals added to the basic alloys as the fourth components or more such as palladium, silver and gold.

Then, a relationship between corrosion resistance and gallium and tin contents of the liquid alloys is discussed. In P2 series, corrosion resistance improves from S28 (x), combination with L28 (83% Ga), and S46 (x), a combination with L9 (75% Ga), to S42 (Δ), a combination with L13 (65% Ga, 12.5% Sn), and S36 (○), a combination with L19 (65% Ga, 15% Sn) respectively.

These results provide the basis for preferable composition of liquid alloys as shown by Zone B in FIG. 1.

In the above examples, any of the supplementary powder additives was of a fine and flaky shape having a good diffusibility into the matrix to effect an improvement in corrosion resistance. If spherical or roundish-irregular shape of supplementary metal powder particles are used, those having a particle size finer or coarser than that of the main metal powder are advantageous in improving the compressive strength, because the packing density can be increased in this case. If supplementary metal powder rich in noble metals is used for a filling material within a limitation in price, the ratio of the supplementary metal powder to the main metal powder should adequately be about 30% or less. In such a case, the supplementary metal powder should preferably be finer than the main metal powder.

In addition to improvements in corrosion resistance and compressive strength as described above, addition of the supplementary metal powder has the secondary effects such as an improvement in workability at mixing and in enlarging allowable limits for powder-liquid ratios.

Furthermore, mixing and filling workability in a dental clinic have been investigated for filling class I to III cavity and MOD cavity. In case of S52, carving time was 2'30" to 4'30" for filling class I to III cavity, and 2'35" to 5'40" for filling MOD cavity. Its rising rate of hardening was also high. Thus, S52 showed workability comparable to conventional amalgams.

At to the rate of hardening, S26 showed Vickers hardness of 70–105 Hv after storage at 37±1° C. for 2 hrs after mixing, and 105–130 Hv 24 hrs after mixing, with a compressive strength of 42–50 kgf/mm². Thus, together with evaluation of other properties described above, the hardened products of the invention are evaluated to be capable of practical use in place of conventional amalgams from clinical viewpoints.

The hardenable mixtures of the invention can be used equally with conventional dental amalgams, since they have good corrosion resistance, hardening properties and mechanical strength equivalent or superior to those of ordinary amalgams meeting the JIS standards, and have good workability in clinical use.

Therefore, the effect of the invention is extremely great since it provides an alternative to using Hg which suffers from environmental pollution and toxicity to a person in the field of dentistry, and can serve a new dental filling materials for practical use in place of conventional amalgams while maintaining the merits of conventional filling materials. Also, the hardenable mixtures of the invention have another advantage as moldable materials, that they can be used for another purpose like cast materials as well as filling materials.

The invention was illustrated above with reference to preferred embodiments, however, various alterations and modifications of the invention can obviously be made within the scope and the spirit of the claims.

What is claimed as new and desired to be secured by Letters Patent of the United States is:

1. A gallium alloy for dental restorations which is hardenable at mouth temperature or around 37° C. or more which comprises:
   (a) a multicomponent liquid gallium alloy;
   (b) a metal or metal alloy powder;
said multicomponent liquid gallium alloy being triturated with said metal or metal alloy powder producing a triturated mixture, said triturated mixture having a heterogeneous structure after hardening and said triturated mixture comprising 9–47% gallium, 1–35% indium, 0.2–38% tin and 1–68% silver, and at least one element selected from the group consisting of 0.4–35% palladium, 0.5–25% copper and 0.4–12% zinc.

2. The gallium alloy for dental restorations of claim 1, said triturated mixture further comprising at least one element selected from the group consisting of gold, platinum and germanium.

3. The gallium alloy for dental restorations of claim 1, wherein said multicomponent liquid gallium alloy comprises 45–85% gallium, 5–40% indium and 1–30% tin.

4. The gallium alloy for dental restorations of claim 3, wherein said multicomponent liquid gallium alloy comprises 49–71% gallium, 13–33% indium and 12–28% tin.

5. The gallium alloy for dental restorations of claim 4, wherein said multi component liquid gallium alloy further comprises 0.01–5% of at least one element selected from the group consisting of silver, palladium, gold, platinum, copper, zinc and germanium.

6. The gallium alloy for dental restorations of claim 3, wherein said multicomponent liquid gallium alloy further comprises 0.01–5% of at least one element selected from the group consisting of silver, palladium, gold, platinum, copper, zinc and germanium.

7. The gallium alloy for dental restorations of claim 1, wherein said metal alloy powder comprises 1–85% silver and at least two elements selected from the group consisting of 1–40% tin, 1–40% palladium, 1–30% copper, 1–15% zinc and 1–25% indium.

8. The gallium alloy for dental restorations of claim 7, wherein said metal alloy powder comprises spherical or near spherical-irregular particles.

9. The gallium alloy for dental restorations of claim 1, wherein said metal alloy powder is used with at least one supplementary powder additive selected from the group consisting of palladium, platinum, gold, silver, copper, tin and powdered alloys containing one or more of said metals, in which said supplementary powder additive has spherical or near spherical-irregular particle shapes having particle sizes different from those of said metal alloy powder.

10. The gallium alloy for dental restorations as claimed in claim 9, wherein said supplementary powder additive has flat or flaky particle shapes.

* * * * *